(12) United States Patent
Park

(10) Patent No.: US 7,334,414 B2
(45) Date of Patent: Feb. 26, 2008

(54) MULTI-FUNCTIONAL CHILD CARE STORAGE

(75) Inventor: Sungwoo Park, Seoul (KR)

(73) Assignee: Daewoo Electronics Corporation, Seoul (KR)

( * ) Notice: Subject to any disclaimer, the term of this patent is extended or adjusted under 35 U.S.C. 154(b) by 80 days.

(21) Appl. No.: 11/360,381

(22) Filed: Feb. 24, 2006

(65) Prior Publication Data
US 2006/0218937 A1   Oct. 5, 2006

(30) Foreign Application Priority Data
Mar. 29, 2005   (KR) ...................... 10-2005-0025776

(51) Int. Cl.
*F25B 21/02* (2006.01)
(52) U.S. Cl. ........................ 62/3.3; 62/457.4; 62/457.5
(58) Field of Classification Search ................... 62/3.3, 62/3.6, 3.61, 457.2, 457.4, 457.5, 457.9
See application file for complete search history.

(56) References Cited

U.S. PATENT DOCUMENTS

| 2,616,269 | A | | 11/1952 | Reynolds | |
| 3,216,204 | A | * | 11/1965 | Milligan et al. | 62/3.2 |
| 5,588,300 | A | * | 12/1996 | Larsson et al. | 62/3.61 |
| 5,970,719 | A | | 10/1999 | Merritt | |
| 6,038,865 | A | * | 3/2000 | Watanabe et al. | 62/3.6 |
| 6,729,144 | B1 | * | 5/2004 | Kupferman | 62/3.6 |

FOREIGN PATENT DOCUMENTS

| GB | 2386938 | 10/2003 |
| JP | 2001-124431 | 5/2001 |

* cited by examiner

*Primary Examiner*—Melvin Jones
(74) *Attorney, Agent, or Firm*—Bacon & Thomas, PLLC

(57) ABSTRACT

A child care storage includes a refrigerating compartment for refrigerating the infant care products by using a thermoelectric element and a warming-in-water compartment for heating the infant care products by warming-in-water; a heat exchanging apparatus for heating the water in the warming-in-water compartment by using the heat produced from a heat-emitting side of the thermoelectric element; and a control unit for controlling temperature in the refrigerating compartment and the warming-in-water compartment.

4 Claims, 7 Drawing Sheets

MULTI-FUNCTIONAL CHILD CARE STORAGE

FIELD OF THE INVENTION

The present invention relates to a multi-functional child care storage; and, more particularly, to a multi-functional child care storage including a plurality of functional compartments for storing or treating infant food or infant products in various ways.

BACKGROUND OF THE INVENTION

In general, a refrigerator is used to keep food or beverage in a refrigerated or frozen state for a long time or to cool them rapidly. The refrigerator includes a freezing compartment and a refrigerating compartment opened or closed by individual front doors. To supply cold air to the freezing compartment and the refrigerating compartment, the refrigerator has a compressor, a condenser, a capillary tube and a cooling device to perform a cooling cycle. The compressor compresses a coolant at a high temperature and pressure, and provides thus compressed coolant to the condenser. Then, the condenser condenses the compressed coolant at a low temperature and pressure by releasing heat of the coolant. The condensed coolant is then converted into a liquid state of a low temperature and a high pressure while it passes through the capillary tube. The low-temperature high-pressure condensed coolant is then directed to the cooling device installed at a rear side of the freezing compartment. The coolant sent to the cooling device is converted into a low-pressure state again while it passes through a coolant pipe in the cooling device, and finally evaporates, thereby reducing the temperature in the freezing compartment and the refrigerating compartment.

Recently, with a rise in the standard of living, there have been increasing demands for diversified types of special-purpose refrigerators. Developed to meet such needs are, for example, a kimchi refrigerator equipped with an evaporation pipe and a heating wire for the ripening of kimchi, a cosmetic cooler for storing cosmetics at a low temperature by cooling a cosmetic storage compartment with a relatively small volume by means of a thermoelectric element, and so forth.

Though such various types of special-purpose refrigerators have been developed and commonly utilized, developments have rarely been made upon a storage apparatus for an exclusive use in baby or child care.

If infant food or infant products such as powdered milk, breast milk, medicine and the like are stored in a conventional household refrigerator, they will be soaked with the odors of other foods stored in the refrigerator. As a result, the quality of the infant food or the infant products will be deteriorated and, even worse, hygienic problems may be resulted. Furthermore, in case of using a microwave to warm up, e.g., milk, the milk has to be warmed up after being taken out of the refrigerator, which is very troublesome. Also, purchasing a heating cabinet to warm up the milk or store the warm milk is not economical because the heating cabinet is just for heating and cannot be utilized for other purposes. Furthermore, since the heating cabinet is designed to be used in commercial environments such as hospitals, pharmacies, restaurants, and so forth, it is not suitable for use in home for the purpose of child care.

Moreover, given that a general household sterilizing device is usually designed to be used in sterilizing kitchenware such as dishware or utensils, using it to sterilize infant products such as feeding bottles, handkerchiefs, toys and the like is not proper.

U.S. Pat. No. 4,909,040 discloses a refrigerator provided with a sterilized storage compartment. Though the refrigerator is capable of improving user's convenience by providing various functions, it does not have features suitable for child care because of a large capacity.

Further, there have been proposed many sterilizing devices for infant products, particularly, baby bottles. One of them is, for example, a sterilizer described in U.S. Pat. No. 5,213,776. However, the sterilizing device is only for disinfecting infant products, and it does not have a storage function for storing therein various infant products appropriately.

Therefore, breaking from the conventional conception of electronic appliances designed and distributed for housewives, it is necessary to develop a product capable of storing baby food or products appropriately in various ways, while reducing power consumption that might be increased due to the implementation of various functions.

SUMMARY OF THE INVENTION

It is, therefore, an object of the present invention to provide a multi-functional child care storage including a plurality of functional compartments for storing or treating infant food or infant products in various ways.

Another object of the present invention is to provide a multi-functional child care storage capable of improving energy efficiency.

In accordance with a preferred embodiment of the present invention, there is provided a child care storage for storing and treating infant care products including a refrigerating compartment for refrigerating the infant care products, a warming-in-water compartment for warming up the infant care products by warming-in-water, a heat exchanging apparatus including a thermoelectric element for absorbing heat at a first side thereof to cool down the refrigerating compartment and emitting the heat thus absorbed at a second side thereof to the warming-in-water compartment, and a control unit for controlling temperature in the refrigerating compartment and the warming-in-water compartment compartment.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, preferred embodiments of the present invention will be described in detail with reference to the accompanying drawings so that they can be readily implemented by those skilled in the art.

Figure 1:
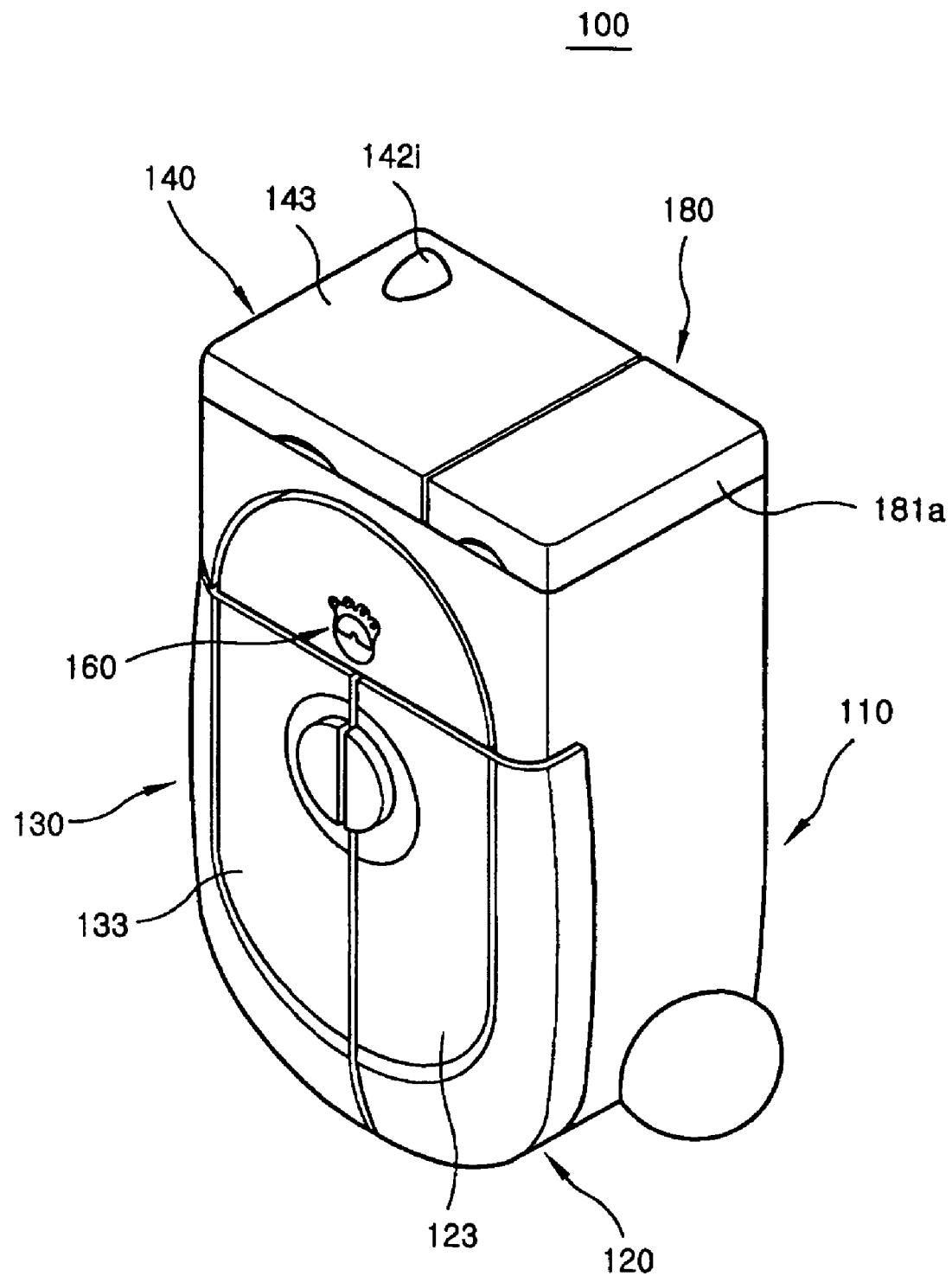
FIG. 1 is a perspective view of a multi-functional child care storage.
Figure 2:
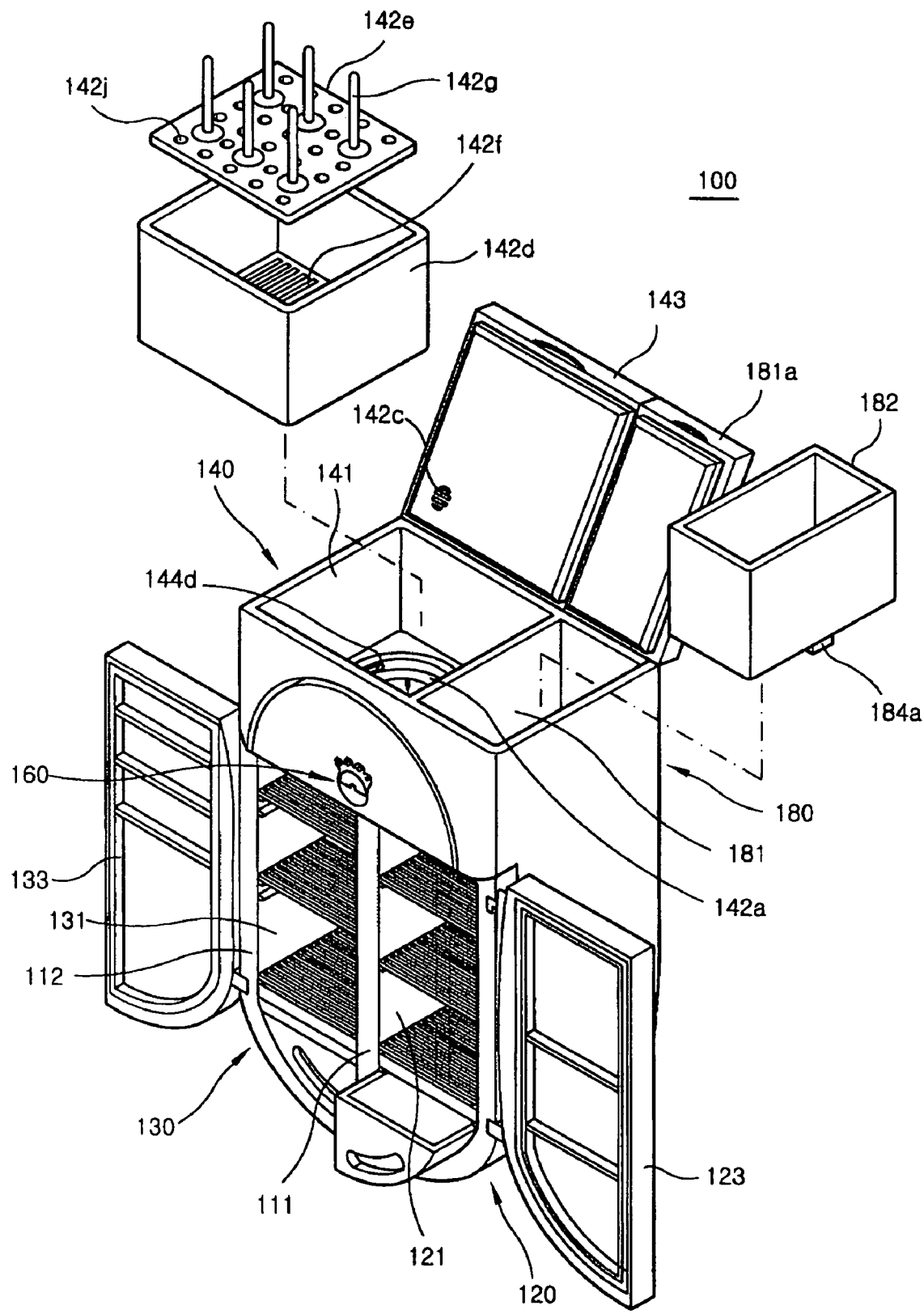
FIG. 2 sets forth a perspective view of the multi-functional child care storage in accordance with the present invention showing a state where its doors are opened.
Figure 3:
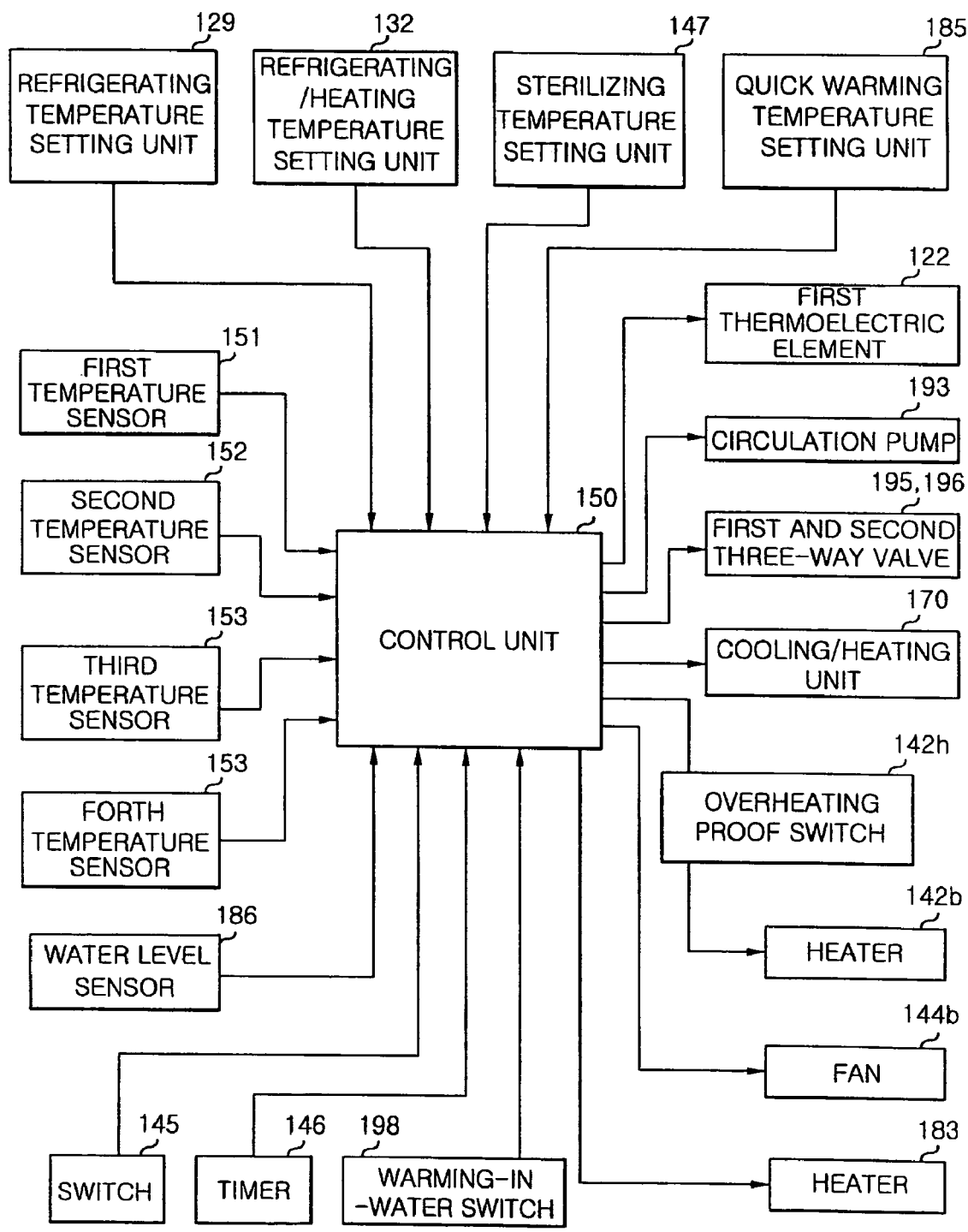
FIG. 3 presents a block diagram for controlling the multi-functional child care storage in accordance with the present invention.

FIG. 1 is a perspective view of a multi-functional child care storage, FIG. 2 presents a perspective view of same showing a state where its doors are opened, and FIG. 3 provides a block diagram for controlling the multi-functional child care storage.

As shown in these figures, the multi-functional child care storage 100 is for storing or treating infant food or infant products in various ways and it includes a plurality of functional compartments in a main body 110 thereof. The functional compartments include a refrigerating compartment 120, a refrigerating/heating compartment 130, a sterilizing compartment 140 and a warming-in-water compartment 180 for refrigerating, refrigerating/heating as necessary, sterilizing and warming-in-water the infant food or products, respectively. Further, the multi-functional child care storage 100 has a control unit 150 for controlling the functional compartments 120, 130, 140 and 180.

The functional compartments include at least one refrigerating compartment 120, at least one refrigerating/heating compartment 130, at least one sterilizing compartment 140, and at least one warming-in-water compartment 180, wherein the number of the refrigerating compartment 120, the refrigerating/heating compartment 130, the sterilizing compartment 140 and/or the warming-in-water compartment 180 can be appropriately increased depending on necessity.

Inside the main body 110, a refrigerating space 121, a refrigerating/heating space 131, a sterilizing space 141 and a warming space 181 are defined by dividing the space inside a wall 112 of the main body 110 by partitions 111.

Figure 4:
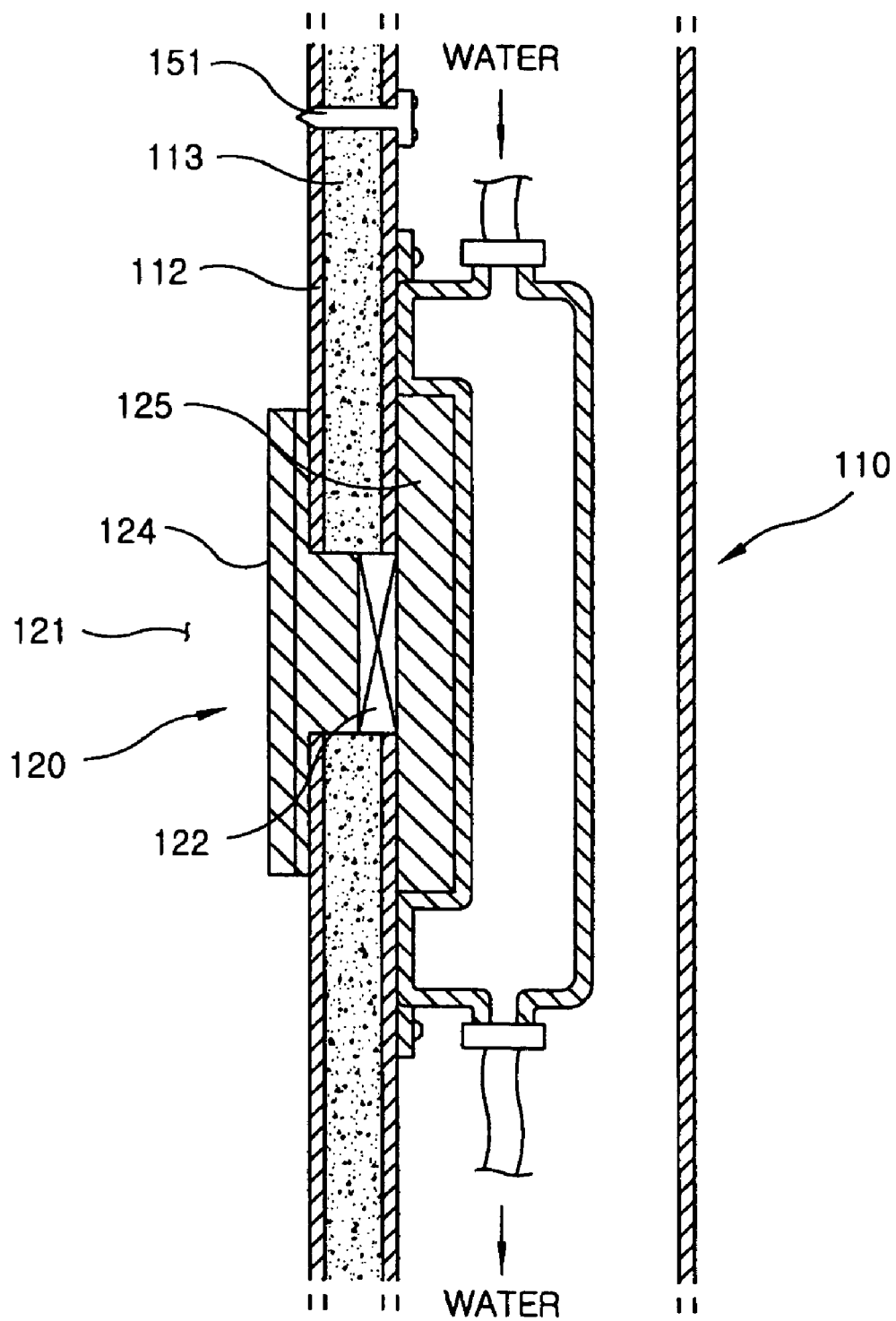
FIG. 4 provides a partial side cross sectional view of the assembly involving a thermoelectric element of a refrigerating compartment in accordance with the present invention.

The refrigerating compartment 120 has a first door 123 for opening or closing the refrigerating compartment 120. Further, as shown in FIG. 4, the first thermoelectric element 122 is installed on the wall 112 lying at the back side of the refrigerating space 121. Depending on the supply of an electric current, the first thermoelectric element 122 absorbs heat at one side, to thereby cool down its circumferential air and dissipate the heat thus absorbed at the other side, to thereby heat its circumferential air. The first thermoelectric element 122 has a heat absorbing plate 124 provided at the side of the refrigerating space 121 for the purpose of cooling the latter. A heat radiating plate 125 is placed at the opposite side from the heat absorbing plate 124. Thus, the first thermoelectric element 122 emits coldness into the refrigerating space 121 through the heat absorbing plate 124 and radiates the heat to the opposite side of the refrigerating space 121 through the heat radiating plate 125.

Furthermore, to allow the cold air from the first thermoelectric element 122 to be diffused rapidly throughout the refrigerating space 121, the heat absorbing plate 124 is formed of metal, e.g., aluminum having a high thermal conductivity and is installed such that it is exposed to the refrigerating space 121. Further, a coldness diffusion plate (not shown) may be additionally installed at the side of the heat absorbing plate 124 and exposed to the refrigerating space 121 so that the coldness emitted from the first thermoelectric element 122 can be rapidly diffused to each and every part of the refrigerating space 121.

Meanwhile, though the heat from the first thermoelectric element 122 can be cooled down by a cooling fan (not shown) after it is emitted through the heat radiating plate 125, the heat is cooled by water by a heat exchanging apparatus 190.

As shown in both FIGS. 2 and 3, the refrigerating/heating compartment 130 has a second door 133 for opening or closing the refrigerating/heating compartment 130. The refrigerating/heating compartment 130 is cooled or heated by a cooling/heating unit 170, wherein the cooling/heating unit 170 is controlled by the control unit 150 such that the refrigerating/heating compartment 130 is maintained at a temperature level set by a refrigerating/heating temperature setting unit 132.

Figure 5:
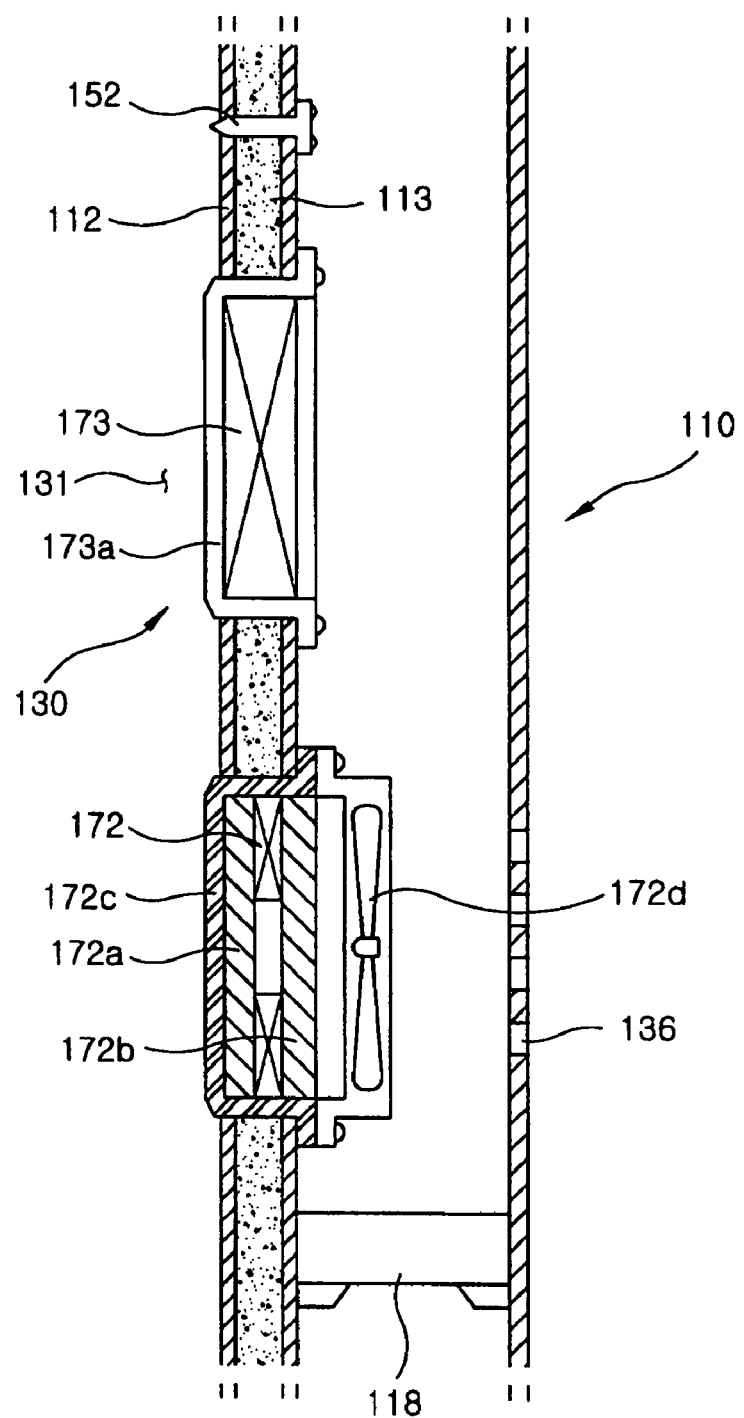
FIG. 5 shows a partial side cross sectional view of a refrigerating/heating compartment of the multi-functional child care storage in accordance with the present invention.

The cooling/heating unit 170 may be implemented by a thermoelectric element or by a combination of a heater and a cooling device to perform both heating and cooling. In accordance with the preferred embodiment of the present invention shown in FIG. 5, the cooling/heating unit 170 includes a second thermoelectric element 172 and a heater 173, each of which is controlled by the control unit 150 such that the refrigerating/heating space 131 is maintained at the temperature level set by the refrigerating/heating temperature setting unit 132.

Like the first thermoelectric element 122, the second thermoelectric element 172 has a heat absorbing plate 172a on one side thereof and a heat radiating plate 172b on the opposite side thereof, and a cold air diffusion plate 172c is installed on the heat absorbing plate 172a such that it is exposed to the refrigerating/heating space 131. Further, a heat radiation fan 172d is installed on the side of the heat radiating plate 172b to discharge the heat from the heat radiating plate 172b to the outside through heat exhaust apertures 136.

The heater 173 is installed at a rear side of the refrigerating/heating space 131, and it serves as a heating block incorporating a heating wire that emits heat when power is supplied thereto. Further, a heat diffusion plate 173a made of, e.g., aluminum having a high thermal conductivity is connected to the heater 173's side facing the refrigerating/heating space 131. The heat diffusion plate 173a is exposed to the refrigerating/heating space 131 to diffuse the heat from the heater 173 into the refrigerating/heating space 131 rapidly.

Figure 6:
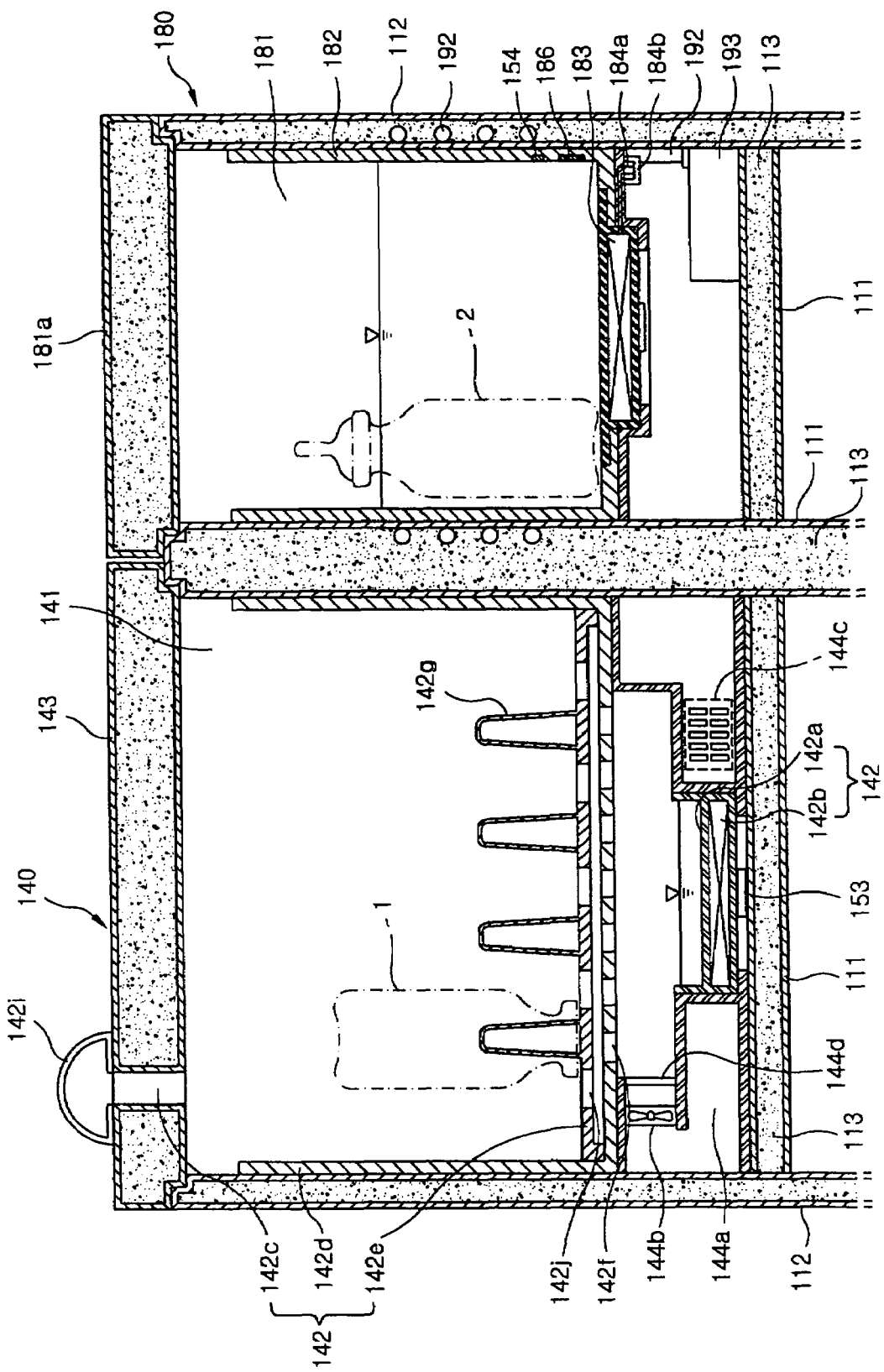
FIG. 6 is a sectional front elevation showing a sterilizing compartment and a warming-in-water compartment of the multi-functional child care storage.

As shown in FIG. 6, the sterilizing compartment 140 is used for sterilizing infant accessories loaded therein with hot steam. The sterilizing compartment 140 includes a steam sterilizing unit 142 for sterilizing infant items such as a baby bottle 1 loaded in the sterilizing space 141 by steam, and drying device 144 for drying the baby bottle 1 after they are sterilized in the sterilizing space 141.

The steam sterilizing unit 142 includes an evaporation vessel 142a disposed at a bottom portion of the sterilizing space 141 to store water therein; a heater 142b installed below the evaporation vessel 142a to heat the evaporation vessel 142a, thus allowing the water in the evaporation vessel 142a to evaporate; and a steam outlet 142c provided in the third door 143 to exhaust the steam from the sterilizing space 141. Moreover, the steam sterilizing unit 142 has an overheating proof switch 142h (not shown in this figure, see FIG. 3) such as a bimetal switch installed at the heater 142b.

The overheating proof switch 142h serves to stop a power supply when the heater 142b is overheated beyond a preset temperature level.

A steam outlet 142c is formed in the main body 110, but in the preferred embodiment, it is formed in the third door 143. Further, a cover 142i is installed at an upper portion of the third door 143 on the discharge side of the steam. The cover 142i allows the steam to be discharged backward, thus preventing a user to contact the steam directly.

The steam sterilizing unit 142 also has a sterilization vessel for loading infant items therein, and is disposed above the evaporation vessel 142a. The sterilization vessel may be formed in various shapes and structures. In the preferred embodiment of the present invention, the sterilization vessel includes a rack 142e for arranging the baby bottle 1 thereon and a rack holder 142d for accommodating the rack 142e therein. The rack holder 142d serves to isolate the baby bottle 1 from the evaporation vessel 142a and is provided with steam passing holes 142f in its bottom surface, wherein the steam passing holes 142f allow the steam to pass therethrough. The rack holder 142d can be readily taken out of the sterilizing space 141 after completing the sterilization of the baby bottle 1. The rack 142e has a plurality of posts 142g on which the infant products such as the baby bottle 1 are to be hung; and multiple steam passing holes 142j.

The drying device 144 includes an air suction duct 144a serving as an air passageway through which exterior air is introduced into the sterilizing space 141; and a fan 144b installed in the air suction duct 144a to blow the exterior air inside the sterilizing space 141. Moreover, to supply clean air to the sterilizing space 141, the drying device 144 has a detachable filter 144c to trap air-borne dusts on the air inlet side of the air suction duct 144a communicated with the main body 110.

The air suction duct 144a is configured such that its end portion 144d on the air outlet side from the fan 144b is adjacent to the evaporation vessel 142a. Accordingly, the heat of the evaporation vessel 142a can be supplied into the sterilizing space 141 by the fan 144b, whereby the drying time can be reduced.

Still referring to FIG. 6, the warming-in-water compartment 180 has the warming space 181 for warming up, e.g., milk in a baby bottle 2. The warming space 181 is formed in the main body 110 by partitions 111 and is opened or closed by a fourth door 181a. A warming vessel 182 is for accommodating water therein and is detachably installed in the warming space 181. The water in the warming vessel 182 is heated by the heat from the first thermoelectric element 122 of the refrigerating compartment 120. The heat of the first thermoelectric element 122 is delivered to the warming vessel 182 by the heat exchanging apparatus 190, which will be disclosed as below.

Figure 7:
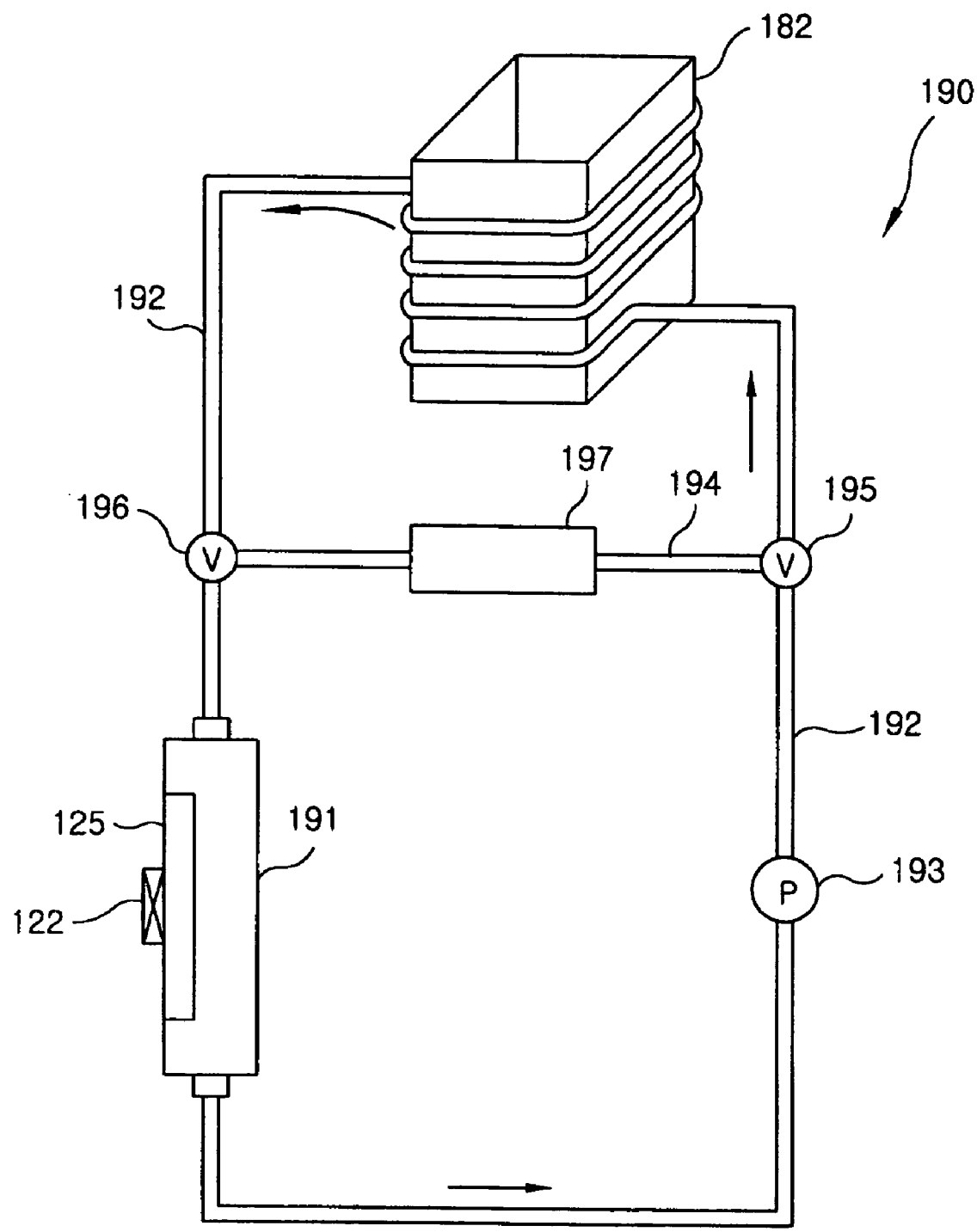
FIG. 7 is a block diagram of a heat exchanging apparatus for warming-in-water in the multi-functional child care storage in accordance with the present invention.

Referring to both FIGS. 4 and 7, the heat exchanging apparatus 190 includes a water jacket 191 installed at the heat radiating plate 125 on the heat-emitting side of the first thermoelectric element 122; a circulation pipe 192 serving as a water circulation path through which warm water from the water jacket 191 is circulated via the warming-in-water compartment 180, during which the warm water is cooled down; and a circulation pump 193 installed on the circulation pipe 192.

The water jacket 191 is installed to surround the heat radiating plate 125 disposed at the first thermoelectric element 122 of the refrigerating compartment 120, so that the water filled in the water jacket 191 is heated by the heat emitted from the heat radiating plate 125.

A part of the circulation pipe 192 is wounded around the warming vessel 182 inside the warming-in-water compartment 180 to heat the warming vessel 182, and both ends of the circulation pipe 192 are connected to the water jacket 191.

The circulation pump 193 pumps up the water in the water jacket 191 such that it is circulated through the circulation pipe 192.

The heat exchanging apparatus 190 serves to supply heat from the first thermoelectric element 122 to the warming-in-water compartment 180, and to cool down the heat from the first thermoelectric element 122. In case that a user don't need to use the warming-in-water compartment 180, it is necessary to stop the supply of the warm water to the warming-in-water compartment 180.

As a measurement to stop the supply of the warm water to the warming-in-water compartment 180, the heat exchanging apparatus 190 has a bypass pipe 194 for allowing the warm water of the water jacket 191 to be circulated without passing through the warming-in-water compartment 180. The bypass pipe 194 is connected to the circulation pipe 192, and a first and a second three-way valve 195 and 196 for shifting the flow path of the warm water are installed at connection points between the bypass pipe 194 and the circulation pipe 192, respectively. Further, a radiator 197 is installed on the bypass pipe 194 to cool down the warm water passing therethrough. Accordingly, when the supply of the warm water to the warming-in-water compartment 180 needs to be stopped, the first and the second three-way valve 195 and 196 are operated by turning off a warming-in-water switch 198 (see FIG. 3) such that the warm water from the water jacket 191 is circulated through the bypass circuit 194. Alternatively, it is possible to configure that the warming-in-water compartment 180 has a separate heater 183 (see FIG. 6) reserved for warming-in-water. In case a heat supply through the heat exchanging apparatus 190 is not possible because the operation of the refrigerating compartment 120 is stopped or the water for the warming-in-water in the warming-in-water compartment 180 needs to be heated rapidly, the warming-in-water can be performed by means of the heater 183. Also, by using the heater 183, a rapid warming-in-water can be carried out.

Referring to FIG. 6, the heater 183 includes a heating block incorporating a heating wire therein and is installed on the bottom portion of the warming vessel 182. Further, both a power supply connector 184a and 184b are configured to couple each other before the warming vessel 182 is inserted in the warming space 181. Thus, when they are coupled, an electric power is supplied to the heater 183. As a result, the warming vessel 182 is heated by the heater 183.

The warming-in-water compartment 180 has a quick warming temperature setting unit 185 (see FIG. 3) to drive the heater 183 and to set temperature needed in case of warming up, e.g., the baby bottle 2 by using the heater 183 under the control of the control unit 150. Moreover, in order to prevent the warming vessel 182 from being overheated due to the lack of water when it is heated by the heater 183, a water level sensor 186 is installed in the warming vessel 182 to detect a water level therein. A detection signal from the water level sensor 186 is sent to the control unit 150, and if the water level in the warming vessel 182 falls below a preset value, the control unit 150 stops the heater 183.

Referring back to FIG. 3, the control unit 150 receives detection signals from a first to a third temperature sensor 151 to 153 installed in the refrigerating compartment 120, the refrigerating/heating compartment 130 and a sterilizing compartment 140, respectively. Then, the control unit 150 controls the operations of the first thermoelectric element 122 in the refrigerating compartment 120, the cooling/heating unit 170 in the refrigerating/heating compartment 130 and the heater 142*b* in the steam sterilizing unit 142 such that the internal temperatures of the refrigerating compartment 120, the refrigerating/heating compartment 130 and the sterilizing compartment 140 are maintained at temperature levels set by a refrigerating temperature setting unit 129, the refrigerating/heating temperature setting unit 132 and a sterilizing temperature setting unit 147, respectively. Also, the control unit 150 controls the fan 144*b* of the drying device 144 depending on the manipulation of the switch 145.

Moreover, the control unit 150 operates the first and the second three-way valve 195 and 196 as the warming-in-water switch 198 is turned on/off to allow the warm water in the water jacket 191 to be supplied to the warming-in-water compartment 180 or to stop the supply of the warm water thereto. In addition, based on a signal from the quick warming temperature setting unit 185 and a detection signal from a fourth temperature sensor 154 for detecting the internal temperature of the warming space 181, the control unit 150 controls the heater 183 such that its temperature is maintained at a temperature value set by the quick warming temperature setting unit 185.

The refrigerating temperature setting unit 129, the refrigerating/heating temperature setting unit 132, the sterilizing temperature setting unit 147, the quick warming temperature setting unit 185, and the switches 145 and 198 are installed at a control panel 160 (see FIG. 1) provided on the front surface of the main body 110.

Below, an operation of the multi-functional child care storage 100 having the above-described configuration will be explained.

In the refrigerating compartment 120, infant food (especially, breast milk), infant medicine, infant cosmetics and so forth are stored. The items loaded in the refrigerating compartment 120 are cooled by cold air diffused throughout the refrigerating space 121 via the heat absorbing plate 124 after being emitted from the thermoelectric element 122.

The refrigerating/heating compartment 130 is controlled by the cooling/heating unit 170 for maintaining the internal temperature of the refrigerating/heating compartment 130 at a temperature level set by the refrigerating/heating temperature setting unit 132. For example, baby food such as vegetables and fruits, baby cosmetics, medicine, tropical fruits, and warm beverage or herbal medicine can be stored at 3° C., to 4° C., 7° C., 10° C., 8 to 12° C., and 35° C., to 40° C., respectively. Further, the refrigerating/heating temperature can be freely adjusted depending on the type of food or products to be stored.

The sterilizing compartment 140 sterilizes the infant accessories such as the baby bottle 1, handkerchiefs and toys loaded in the sterilizing space 141 by means of the steam sterilizing unit 142, that is, by using the steam obtained by evaporating the water in the evaporating vessel 142*a* by the heater 142*b*. Also, the sterilizing compartment 140 dries the sterilized items by the air blown thereto by the fan 144*b* of the drying device 144.

The warming-in-water compartment 180 is heated by the heat emitted from the heat-emitting side of the first thermoelectric element 122 of the refrigerating compartment 120, wherein the heat of the first thermoelectric element 122 is delivered to the warming-in-water compartment 180 by the heat exchanging apparatus 190. At this time, the water in the warming vessel 182 is heated by the warm water supplied thereto through the circulation pump 193. Thus, the infant accessories stored in the sterilizing compartment 140 can be warmed up easily, and breast milk, water, beverages, herbal medicine and the like can also be conveniently warmed up by warming-in-water. Meanwhile, when the warming-in-water compartment 180 is not used, the first and the second three-way valve 195 is operated by turning off the warming-in-water switch 198, whereby the warm water gets circulated through the bypass pipe 194 without passing through the warming-in-water compartment 180. At this time, the warm water is cooled down while it passes through the radiator 197 installed on the bypass pipe 194, so that the heat from the first thermoelectric element 122 can be cooled down continuously.

Meanwhile, when the operation of the refrigerating compartment 120 is stopped or the water for the warming-in-water in the warming-in-water compartment 180 needs to be heated rapidly, the water in the warming vessel 182 is heated by the heater 183 by manipulating the quick warming temperature setting unit 185. Here, the temperature for the warming-in-water can be freely adjusted by using the quick warming temperature setting unit 185. Furthermore, since the heater 183 is driven while the water level in the warming vessel 182 is being monitored by the water level sensor 186, the heater 183 can be prevented from being overheated.

In accordance with the preferred embodiment of the present invention described above, infant food or products can be stored or treated in various ways in a single apparatus including various functional compartments such as the refrigerating compartment and the warming-in-water compartment. Therefore, the convenience of user can be improved, and the time required for child care can be reduced. Moreover, by heating the water in the warming-in-water compartment by using the heat from the thermoelectric element installed in the refrigerating compartment, energy efficiency can be improved. Also, depending on necessity, the temperature of the water in the warming-in-water compartment can be rapidly increased by operating the heater additionally installed in the warming-in-water compartment.

While the invention has been shown and described with respect to the preferred embodiments, it will be understood by those skilled in the art that various changes and modifications may be made without departing from the spirit and scope of the invention as defined in the following claims.

What is claimed is:

1. A child care storage for storing and treating infant care products, comprising:
   a refrigerating compartment for refrigerating the infant care products;
   a warming-in-water compartment for warming up the infant care products by warming-in-water;
   a heat exchanging apparatus including a thermoelectric element for absorbing heat at a first side thereof to cool down the refrigerating compartment and emitting the heat thus absorbed at a second side thereof to the warming-in-water compartment; and
   a control unit for controlling temperature in the refrigerating compartment and the warming-in-water compartment compartment.

2. The child care storage of claim 1, wherein the heat exchanging apparatus includes:
   a heat radiating plate, installed at the second side, for dissipating the heat from the thermoelectric element;
   a water jacket, installed at the heat radiating plate, for heating water therein by the heat from the heat radiating plate;

a circulation pipe, extended to the warming-in-water compartment, through which the warm water from the water jacket to be circulated via the warming-in-water compartment in order to warm up the infant care products by warming-in-water; and a circulation pump for pumping up the warm water in the water jacket to be circulated through the circulation pipe.

3. The child care storage of claim 2, wherein the heat exchanging apparatus further includes:

a bypass pipe connected to the circulation pipe, for guiding the warm water from the water jacket to be circulated without passing through the warming-in-water compartment;

a first and a second three-way valve connected at connection points between the bypass pipe and the circulation pipe, for shifting a flow path of the warm water;

a radiator installed on the bypass pipe, for cooling the warm water passing therethrough; and a warming-in-water switch for turning on/off the operations of the first and the second three-way valve.

4. The child care storage of claim 3, wherein the warming-in-water compartment includes:

a warming vessel, detachably installed in the warming-in-water compartment, for storing the water therein to be heated by the warm water through the circulation pipe; and a heater, installed in the warming-in-water compartment, for heating the water therein if there is no heat supply through the heat exchanging apparatus.

* * * * *